US008984967B2

(12) United States Patent
Zhang et al.

(10) Patent No.: US 8,984,967 B2
(45) Date of Patent: Mar. 24, 2015

(54) METHOD FOR SAMPLING JOINTED ROCK MASS

(75) Inventors: Chunsheng Zhang, Hangzhou (CN); Ning Liu, Hangzhou (CN)

(73) Assignee: Powerchina Huadong Engineering Corporation Limited, Hangzhou, Zhejiang Province (CN)

( * ) Notice: Subject to any disclaimer, the term of this patent is extended or adjusted under 35 U.S.C. 154(b) by 112 days.

(21) Appl. No.: 13/614,195

(22) Filed: Sep. 13, 2012

(65) Prior Publication Data

US 2013/0247693 A1    Sep. 26, 2013

(30) Foreign Application Priority Data

Sep. 28, 2011    (CN) .......................... 2011 1 0298432

(51) Int. Cl.
*G01N 1/04* (2006.01)
*G01N 1/08* (2006.01)

(52) U.S. Cl.
CPC ... *G01N 1/04* (2013.01); *G01N 1/08* (2013.01)
USPC .................. 73/863.11; 73/864.44; 73/864.43

(58) Field of Classification Search
USPC ............... 73/863.11, 864.41–864.51, 152.02, 73/152.07, 152.39
See application file for complete search history.

(56) References Cited

U.S. PATENT DOCUMENTS

| 3,842,608 | A | * | 10/1974 | Turzillo | ......................... 405/236 |
| 3,978,932 | A | * | 9/1976 | Mielke | .......................... 175/249 |
| 2012/0111635 | A1 | * | 5/2012 | Caffell et al. | ................... 175/58 |

* cited by examiner

*Primary Examiner* — Peter Macchiarolo
*Assistant Examiner* — Anthony W Megna Fuentes
(74) *Attorney, Agent, or Firm* — PROI Intellectual Property US; Klaus Michael Schmid

(57) ABSTRACT

The present disclosure relates to a method for sampling rock mass, especially jointed rock mass. The present disclosure provides a simple and convenient method for sampling jointed rock mass to prevent the rock sample from being disturbed and damaged during sampling and accordingly resulting in opening of the weak structural planes, to therefore obtain rock specimen correctly reflecting the basic physical and mechanical characteristics of rock mass comprising integral fissure network. The method for sampling jointed rock mass of the present disclosure comprises the following steps: Step a: Siting; Step b: Drilling; Step c: Protecting; and Step d: Sampling. The method is suitable for determining the basic mechanical properties of the rock mass and for assessing the stability of caverns in jointed rock mass.

5 Claims, 3 Drawing Sheets

METHOD FOR SAMPLING JOINTED ROCK MASS

TECHNICAL FIELD

This disclosure relates to a method for sampling rock mass, especially jointed rock mass. By sampling the jointed rock mass, rock samples with integral fracture network can be acquired and accordingly basic lab tests for the rock mass can be carried out. In addition, the method can be directly used to determine the basic mechanical properties of the rock mass and to assess the stability of caverns in jointed rock mass.

BACKGROUND

In the long geological evolution, intact rock has been subjected to various structural geological actions, resulting in all kinds of weak structural planes. Moreover, these weak structural planes greatly reduce the strength of the rock, even directly affecting the stability of the whole underground caverns. Therefore, how to obtain a rock sample representing the basic physical and mechanical characteristics of the rock mass for lab tests so that related tests for the rock sample can be conducted is a problem to be solved.

At present, rock samples used for lab tests are mainly intact rock, and few lab tests are carried out for the rock mass. Even if tests of the rock mass with cracks are conducted, the tests are restricted to only a single or two discrete cracks and are limited to the rock mass of a small scale. There is currently no way to get a large scale rock mass comprising integral fracture network; this results in little understanding of the physical and mechanical properties of the rock mass and a lack of direct testing information for evaluating the overall stability of excavated cavern in jointed rock mass.

SUMMARY

The present disclosure provides solutions to at least one or more of the following technical problems: offering a simple and convenient method for sampling jointed rock mass to solve the above-mentioned problems so as to prevent the rock sample from being disturbed and damaged during sampling and accordingly resulting in opening of the weak structural planes, and acquiring rock specimen correctly reflecting the basic physical and mechanical characteristics of rock mass comprising integral fissure network.

The present disclosure provides a method for sampling jointed rock mass, the method comprising the following steps:

Step a: Siting: selecting a sampling position and removing a surface layer of the rock mass till intact rock mass is exposed;

Step b: Drilling: drilling at the selected position with a driller to form a columnar rock sample which is connected to the rock mass only at a bottom of the rock sample, and in the meantime fill water into a 5 mm wide cylindrical trepanning between the rock sample and its surrounding rock masses;

Step c: Protecting: heating a prefabricated transparent cylindrical PVC film sleeve with a wall thickness of 3 mm and an inner diameter slightly less than the outer diameter of the rock sample to make it expand, and covering the rock sample with the sleeve;

Step d: Sampling: removing the rock mass around the rock sample after the sleeve is cooled, applying one or more ring protectors on a surface of the sleeve, covering a top portion of rock sample with plastic foam to avoid damage in transit, and separating the rock sample from the rock mass. After the rock sample is separated from the rock mass, the rock sample may be covered with plastic foam so as to prevent air contact and to prevent its mechanical properties from being affected, and a bottom of the rock sample may be covered with prepared plastic foam so as to protect the integrity of ends of the rock sample.

In the water filling process of step b, the rock sample may be kept under a hydrostatic pressure state with a hydrostatic head of 1 m.

The method provides at least the following advantage: Upon completion of drilling, a prefabricated transparent PVC film sleeve is heated with a wall thickness of 3 mm to make it expand, and then it is inserted into the trepanning and the rock sample is covered coaxially with the PVC sleeve; after the PVC sleeve is cooled it clings tightly to the rock sample and exerts certain pressure on the rock sample without using adhesives. Hence, separation of the weak structural planes due to disturbances in the follow-up sampling procedure can be avoided and the integrity of the rock sample comprising fracture network can be ensured, which provide a reliable basis for evaluating the physical and mechanical properties of the rock mass.

DESCRIPTION OF EMBODIMENTS

Figure 1:
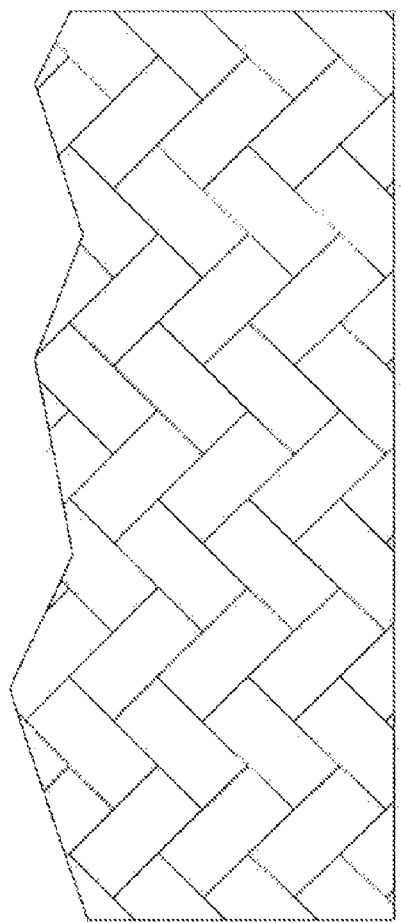
FIG. 1 is a diagrammatic sketch of Step a of the method: selecting a position for sampling.
Figure 2:
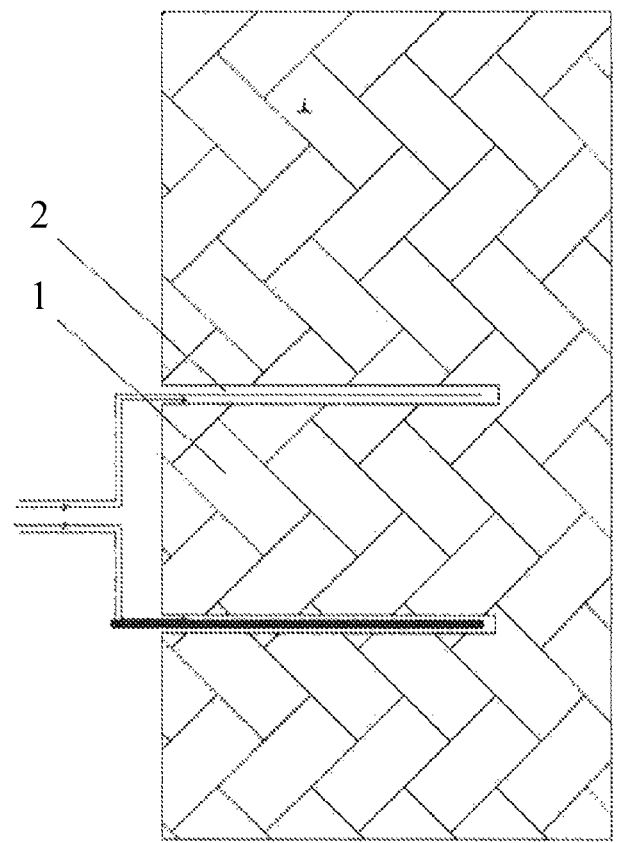
FIG. 2 is a diagrammatic sketch of Step b of the method: drilling and water filling.
Figure 3:
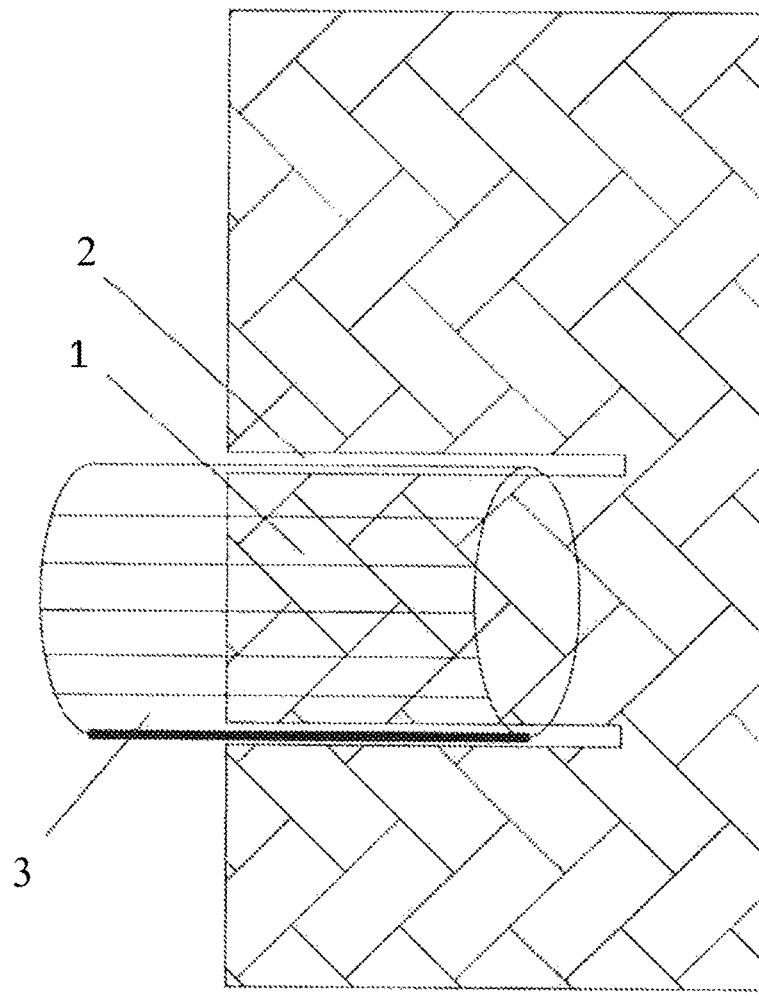
FIG. 3 is a diagrammatic sketch of Step c of the method: applying a film sleeve.
Figure 4:
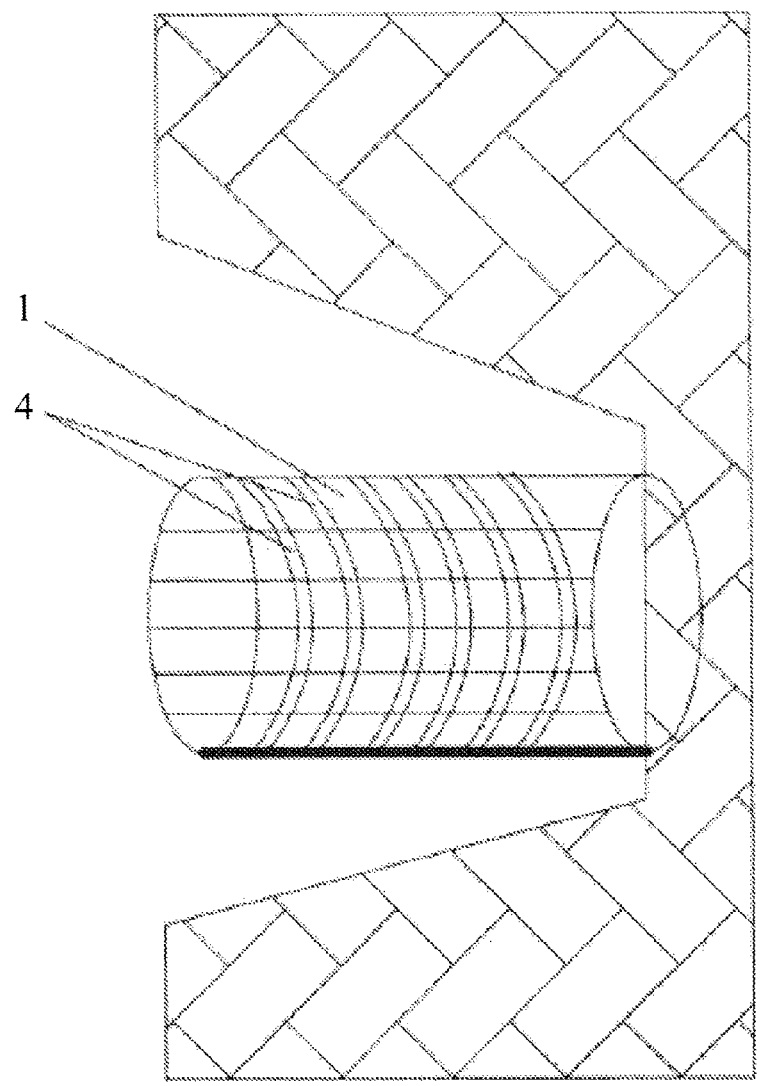
FIG. 4 is a diagrammatic sketch of Step d of the method: sampling and protecting measures.

As shown in FIGS. 1-4, the steps of an embodiment of the method are as follows:

Step a. selecting a position for sampling; the rock mass condition at the selected position should be preferably representative and facilitate drilling. And then removing a surface layer until intact rock mass is exposed.

Step b. drilling at the selected sampling position with a driller, such as an overcore (a tubular drilling tool); at the same time filling water into a tubular trepanning (2) formed in drilling through the cavity of the drilling tool (namely, the aforesaid driller, the same below) to ensure proper water circulation in the trepanning (2). The hydraulic head is usually 1 m so as to facilitate drilling and washing away the surrounding loose rock mass as well as flushing mud and sand produced in drilling out of the rock mass. When the drilling depth meets a requirement, a columnar rock sample (1) is formed in the rock mass; at this time the driller may be taken out from the trepanning (2), and the rock sample (1) is left in its original position, i.e., the rock sample links with the rock mass only at the bottom of the rock sample (1), and at the same time water filling into the trepanning (2) may be stopped. The trepanning (2) formed in drilling is 5 mm wide, namely, the distance between the circumferential surface of the rock sample (1) and the surrounding rock mass is 5 mm. During drilling, the driller shall preferably be kept stably until it can move around the rock sample (1) smoothly. At the same time, in the water filling process, efforts should be made to let the rock sample (1) under a hydrostatic pressure state so as to protect the rock sample from breaking and damaging.

Step c. protecting the rock sample: heating (in this embodiment, by means of hot water of 70-90° C.) a prefabricated transparent cylindrical PVC film sleeve (3) with a wall thickness of 3 mm and an inner diameter slightly smaller (the difference may be about 5 mm) than the external diameter of the rock sample (1) to make it expand, and then inserting the PVC film sleeve into the trepanning (2), covering the rock sample (1) coaxially. After the thin sleeve (3) is cooled, it clings to the rock sample (1) tightly and make it isolated from the surrounding rock mass and the sleeve can exert certain pressure on the rock sample (1) so as to protect the integrity of the rock sample (1) and to minimize the impact of external disturbances on the rock sample (1).

Step d. sampling: removing the rock mass around the rock sample (1), and applying one or more ring protectors (4) on a surface of the sleeve (3), the ring protectors should preferably be applied on the whole section of the rock sample (1) and not just on certain portions of the whole section of the rock sample (1), so as to provide better protection for the rock sample (1), but exertion of excessive pressure should be avoided to prevent the rock sample (1) from being damaged. At the same time, covering a top portion of the rock sample (1) with plastic foam so that the mechanical properties of the rock sample (1) will not be affected due to air contract. In addition, ends of the rock sample (1) are relatively brittle and unnecessary cracks are liable to happen in transit and processing of the rock sample; therefore, the ends should be protected carefully. By covering the rock sample (1) with plastic foam, damages of the rock sample (1) which can occur in transit can be effectively avoided. Then separating the rock sample (1) from the rock mass manually along the weak structural plane. After separating the rock sample from the rock mass, covering the sleeve (3) and the ring protectors (4) tightly with plastic foam to stop the rock sample (1) from contacting air and to prevent its mechanical properties from being affected and consequently to prevent the test result from being affected. Additionally it can also be taken as a measure for the protection of the integrity of the rock sample (1). Finally, covering the bottom of the rock sample (1) with prepared plastic foam to protect the integrity of its ends.

What is claimed is:

1. A method for sampling jointed rock mass comprising the following steps:
    a. selecting a sampling position and removing a surface layer of the rock mass till intact rock mass is exposed;
    b. drilling at the selected position with an overcore to form a columnar rock sample which is connected to the rock mass only at a bottom of the rock sample, and at the same time filling water into a 5 mm wide cylindrical trepanning between the rock sample and its surrounding rock masses;
    c. heating a prefabricated transparent cylindrical PVC film sleeve with a wall thickness of 3 mm and an inner diameter less than an outer diameter of the rock sample so as to make the sleeve expand, and covering the rock sample with the sleeve; and
    d. removing the rock mass around the rock sample after the sleeve is cooled such that the rock sample is exposed, applying one or more ring protectors on a surface of the sleeve, covering a top portion of the rock sample with plastic foam, and separating the rock sample from the rock mass.

2. The method according to claim 1, wherein in the water filling process of step b, the rock sample (1) is kept under a hydrostatic pressure state with a hydrostatic head of 1 m.

3. The method according to claim 1, further comprising the steps of: after the rock sample (1) is separated from the rock mass, covering the rock sample (1) with plastic foam to prevent air contact; and covering the bottom portion of the rock sample (1) with plastic foam.

4. The method according to claim 2, further comprising the steps of: after the rock sample (1) is separated from the rock mass, covering the rock sample (1) with plastic foam to prevent air contact; and covering the bottom portion of the rock sample (1) with plastic foam.

5. The method according to claim 1, wherein said inner diameter of said prefabricated transparent cylindrical PVC film sleeve is 5 mm less than said outer diameter of said rock sample.

* * * * *